United States Patent [19]

Milchanoski et al.

[11] Patent Number: 5,780,248

[45] Date of Patent: Jul. 14, 1998

[54] FOIL SEALED CASSETTE FOR AGGLUTINATION REACTIONS AND LINER THEREFOR

[75] Inventors: Walter Milchanoski, Milford; Milan Jorik, Bridgewater; Kathleen J. Reis, Milford; Diane E. Bechtold, Green Brook, all of N.J.; Linda Davis, Doylestown, Pa.; Thomas M. Setcavage, Milford, N.J.; Donald M. Davies, Unionville, Va.

[73] Assignee: Ortho Diagnostic Systems, Inc., Raritan, N.J.

[21] Appl. No.: 595,719

[22] Filed: Feb. 2, 1996

(Under 37 CFR 1.47)

Related U.S. Application Data

[63] Continuation-in-part of Ser. No. 93,106, Jul. 16, 1993, Pat. No. 5,491,067, which is a continuation of Ser. No. 92,157, Jul. 15, 1993, abandoned.

[51] Int. Cl.$^6$ ............................ G01N 33/50; G01N 33/558
[52] U.S. Cl. ............................ 435/7.25; 422/58; 422/59; 422/101; 422/102; 435/287.1; 435/287.2; 435/288.1; 435/288.4; 435/288.6; 435/810; 436/514; 436/536; 436/538; 436/541; 436/809; 436/810
[58] Field of Search ............................ 422/58, 59, 101, 422/102; 435/287.1, 287.2, 288.1, 288.4, 288.6, 810, 7.25; 436/514, 536, 538, 541, 809, 810

[56] References Cited

U.S. PATENT DOCUMENTS

| | | | |
|---|---|---|---|
| 4,111,754 | 9/1978 | Park | 195/127 |
| 4,895,706 | 1/1990 | Root et al. | 422/102 |
| 4,948,564 | 8/1990 | Root et al. | 422/101 |
| 5,035,866 | 7/1991 | Wannlund | 422/102 |

FOREIGN PATENT DOCUMENTS

| | | | |
|---|---|---|---|
| 0 204 045 | 12/1986 | European Pat. Off. | G01N 33/86 |
| 0 485 228 A1 | 5/1992 | European Pat. Off. | G01N 33/53 |
| 0 634 215 A2 | 1/1995 | European Pat. Off. | B01L 3/00 |
| WO 90/11368 | 10/1990 | WIPO | C12Q 1/56 |
| WO 92/08479 | 5/1992 | WIPO | A61K 37/22 |

OTHER PUBLICATIONS

Millipore Catalog (1991-1992), pp. 223 and 225.

*Primary Examiner*—Christopher L. Chin
*Attorney, Agent, or Firm*—Catherine Kurtz Gowen

[57] ABSTRACT

A vessel for conducting blood cell agglutination assays is disclosed. A barrier retains reactants in an upper chamber during incubation, then, in response to a force, permits reagents to enter a lower chamber containing a matrix for separating agglutination.

10 Claims, 7 Drawing Sheets

FOIL SEALED CASSETTE FOR AGGLUTINATION REACTIONS AND LINER THEREFOR

COPENDING APPLICATION DATA

This application is a continuation-in-part of U.S. Ser. No. 08/093,106, filed Jul. 16, 1993, now U.S. Pat. No. 5,491,067, which is a continuation of U.S. Ser. No. 08/092,157, filed Jul. 15, 1993, now abandoned.

BACKGROUND OF THE INVENTION

This invention relates to the field of agglutination assays, and particularly to vessels useful for conducting agglutination assays and separating agglutinates.

Blood group serology requires the determination of blood cell compatibility between a blood donor and patient recipient before a transfusion or organ transplant involving the patient. Blood cell compatibility is determined by the absence of immunological reaction between antibodies contained in the blood serum of a patient and antigens present on blood cells from the donor.

Many different blood group antigens are found on the surface of red blood cells of every individual. Blood grouping is generally the process of testing red cells to determine which antigens are present and which are absent. This is generally accomplished by using antibodies of known specificity.

For detecting antibodies in the serum or plasma of a patient, reagents containing blood cells having known antigens are mixed with a serum sample. The reactants are incubated for a period of time sufficient to permit agglutination of the red blood cells, which occurs when antibodies against those antigens are present. The mixture is then centrifuged, and if agglutinated blood cells are present, such agglutinates are clearly visible at the bottom of the reaction vessel, thus indicating the presence of antibodies in the sample directed against the known antigens on the red blood cells. If no antibodies are present in the sample directed against the known antigens on the red blood cells, agglutination does not occur, and this is indicated by the absence of agglutinated red cells after centrifugation.

Recently, systems have been developed in which the agglutination reaction is carried out in one portion of a vessel, and separation of agglutinated red cells is accomplished in another portion of the same vessel using a matrix which separates agglutinated cells from other components in the reagent/sample mixture. One such system is disclosed and described in co-pending U.S. patent application Ser. Nos. 08/407,747, and 08/112,402, which are continuations of U.S. Ser. No. 08/023,500, now abandoned, which applications are commonly owned by the owner of the subject application. The contents of each of these applications are hereby incorporated by reference herein. Agglutination reaction and separation vessels according to the present invention, and which are also useful in the inventions disclosed in the aforementioned applications, are manufactured and sold by Ortho Diagnostic Systems Inc., Raritan, N.J., under the trademark BIOVUE™. Such reaction vessels are in the form of a column having an upper chamber and a lower chamber wherein the upper chamber is of a wider diameter than the lower chamber. The lower chamber contains a matrix for separating agglutinated cells from non-agglutinated cells. The diameter of the lower chamber is narrow enough such that when reagents and samples are added to the upper chamber, typically using a pipette, the reagents and samples remain in the upper chamber, and do not enter into the lower chamber, unless an additional force is applied.

An indirect antiglobulin test, known as the Coombs test, is a blood test used to determine whether there are IgG antibodies in a patient's serum to specified antigens on the surface of red blood cells. In the Coombs test, serum is incubated in the presence of reagent red cells to allow the antibodies to bind to antigens on the surface of the red cells. These IgG antibodies most often do not, by themselves, agglutinate the red cells, or only agglutinate them insufficiently to be detected visually by conventional techniques. Addition of a second antibody directed to human IgG is usually necessary to facilitate visible agglutination.

In red cell typing, a blood test used to determine whether certain antigens are present on the surface of red blood cells, the red cells being analyzed are added to the upper chamber followed by application of force such as, for example, centrifugal force which moves them into the lower chamber containing antibodies to particular red cell antigens and the separation matrix. If the red cells have the antigen(s) on their surface to combine with the specific antibodies in the lower chamber, agglutinates will form and be separated by the matrix.

In other types of blood assays, such as reverse typing where directly agglutinating antibodies for red cell antigens in a patient's serum are being assayed, a patient's serum and reagent red blood cells with known antigens on their surface are added to the upper chamber and force, such as, for example, centrifugal force is applied to move the reactants into a lower chamber which contains a liquid medium and separation matrix but no antibody. In this assay the presence of directly agglutinating antibody in the patient's serum would produce agglutinates which would be separated by the matrix.

In another type of blood assay, reagent antibody with a known specificity for a red cell antigen would be deposited into the upper chamber, together with patient's red cells. If the reagent antibody is a directly agglutinating antibody, force, such as for example, centrifugal force would be applied without prior incubation and the contents would be forced into the lower chamber containing separation matrix in aqueous solution. Agglutinates would then be separated by the matrix. Alternatively, patient's red cells are deposited into the upper chamber and IgG reagent antibody with known specificity is added, followed by incubation to allow the antibody to attach to presumptive antigens on the surface of the red cells. After incubation, force, such as for example, centrifugal force is applied to move the reactants into the lower chamber which contains separation matrix and anti-IgG antibodies specific for the IgG reagent antibody used to incubate red cells in the upper chamber. If the reagent antibody is present on the surface of the patient's cells, the anti-IgG antibody in the lower chamber would facilitate the formation of agglutinates which would be separated by the matrix.

After the sample and reagents have been allowed to incubate for a sufficient period of time to permit either direct agglutination, as in the case of a red cell typing test, an antibody-antigen reaction, as in the case of a Coombs test, the reaction vessel is subjected to pressure, for example, via centrifugation such that the reactants are expelled into the lower portion of the column and onto the separation matrix. As a result of the centrifugation, unagglutinated materials migrate down through the separation matrix while agglutinated cells remain on top of the separation matrix or distributed within the matrix depending on the degree of agglutination. Stronger agglutination reactions result in the cells remaining towards the upper portion of the separation matrix while weaker agglutination reactions result in distribution of agglutinates at various distances from the top of the matrix.

Retention of the sample and reagents in the upper portion of the column during the incubation phase is the result of surface tension across the top margin of the lower portion of the column where the diameter is reduced relative to the upper portion. Two potential sources of error in conducting an assay using this column have been identified. First, if reagents and sample are pipetted directly down the center of the reaction chamber with excessive force, the reactants may be deposited directly to the top of the separation matrix in the lower chamber and not retained in the upper chamber during the incubation phase. Thus, the reactants will begin to enter the separation matrix prior to the completion of agglutination. Second, there is potential that the diluent or solution which contains the separation matrix may enter the upper chamber. This can occur through splashing or other disturbance, for example, during shipping and handling of the vessels. In some cases where the solution or diluent containing the separation matrix also contains antibodies or other reagents which directly affect the result of a test, such splashing can result in cross-contamination of columns with certain reagents from other columns. This may occur when the user inserts a pipette tip into the reaction chamber, contaminating the tip with splashed reagent, which may then be transferred to another vessel by the pipette. This may lead to false results in the agglutination assay.

Thus, it is an object of the present invention to provide an improved mechanism for maintaining separation of sample and reagents during the incubation phase of an agglutination assay. It is a further object of the invention to provide means for preventing displacement of materials contained in the lower portion of the column.

SUMMARY OF THE INVENTION

The present invention provides an improved vessel for conducting an agglutination reaction and separating agglutinates. The vessel comprises an upper chamber which holds the reactants, a lower chamber in which agglutinates are separated, and a barrier means separating the chambers, which is capable of retaining reactants in the upper chamber prior to introduction of contents of the upper chamber to the separation matrix, and permitting the contents of the upper chamber to pass from the upper chamber to the lower chamber when a force (i.e., greater than atmospheric pressure) is applied to the barrier. In a preferred embodiment, the barrier comprises a constricted passageway between the upper and lower chambers. Such a constricted passageway can be accomplished by an insert having a constricted aperture, by a crimp, or by an insert having a spiral or other similar geometry which may be either molded with or inserted between the upper and lower chambers during manufacture. Such an insert provides a physical barrier that reduces the size of the aperture between the lower chamber and upper chamber, enhancing prevention of contamination of the upper chamber with contents of the lower chamber. Further, the insert also enhances separation of sample and reagents during incubation. When the insert is a spiral, the passageway described by the threads, center shaft and column walls of the spiral are small enough to retain fluid in the upper chamber under normal gravity and atmospheric pressure. For instance, the diameter of the spiral insert is in the range of from about 0.110 to 0.140 inch. The diameter of the spiral insert shaft is about 0.030 to 0.090 inch. The spiral insert has about 6 to 30 threads per inch.

The constricted passageway may also be provided by sonic welding of the column which is done following loading the column with reagents. The passageway may further contain a barrier in the form of a diaphragm. In this embodiment, the diaphragm has a center perforation small enough to retain fluid in the upper chamber under normal gravity and atmospheric pressure. The diaphragm is preferably silicone rubber. The passageway may further contain a barrier in the form of a porous plug. The porous plug has passageways through it small enough to retain fluid in the upper chamber under normal gravity and atmospheric pressure. The porous plug is preferably polypropylene.

In yet another embodiment, the invention comprises a liner which takes the form of a conical member having an aperture through a narrowed apex. When placed atop and extending into a reaction vessel column prior to pipetting of specimen into the vessel, such liner will prevent cross-contamination of diluent or solution of one vessel from entering another vessel which cross-contamination might otherwise occur during such pipetting. Said liner is conveniently inserted atop the column by the end-user prior to pipetting of reagents. The liner may take the form of a single unit having six conical members or cells arranged side-by-side; the total area and shape of the liner is the same as that of the BIOVUE™ cassette top side.

The liner comprises a body and at least one conical member depending therefrom, wherein said conical member has an aperture at a narrowed apex thereof, and wherein said conical member has sealing means located at a position spaced from said narrowed apex. The conical member comprises a first end comprising said narrowed apex and a second end spaced therefrom adjacent to the body, wherein said sealing means is located at or adjacent to the second end. The sealing means comprises an o-ring surrounding said conical member, and the o-ring may be integral with said conical member. In a preferred embodiment, the liner has six conical members linearly depending from the body, and the liner is sized to fit in the reaction vessels of the cassette. The liner is preferably acrylic.

The invention further contemplates a foil sealed cassette comprising six reaction vessels linearly arranged therein, and a liner comprising a body and six conical members linearly depending therefrom, wherein the conical members comprise a narrowed apex adapted to puncture said foil seal, and when inserted such liner is frictionally engaged in said cassette so as to seal a junction between the cassette and the liner. The means for sealing the junction is o-rings surrounding each of the conical members and preferably integral with each of the conical members.

DETAILED DESCRIPTION OF THE INVENTION

In accordance with the present invention, vessels for conducting agglutination reactions and separating agglutinates will be described in terms of various embodiments. Certain embodiments of the invention may be clearly understood through the description of agglutination reaction and separation vessels manufactured and sold in cassette form by Ortho Diagnostic Systems Inc., Raritan, N.J., under the trademark BIOVUE™.

Vessels of the present invention may be manufactured from any suitable material which will not interfere with the agglutination reaction or separation, an visualization of results, such as glass or various plastics. In a preferred embodiment, the vessels are made from polypropylene.

Figure 1:
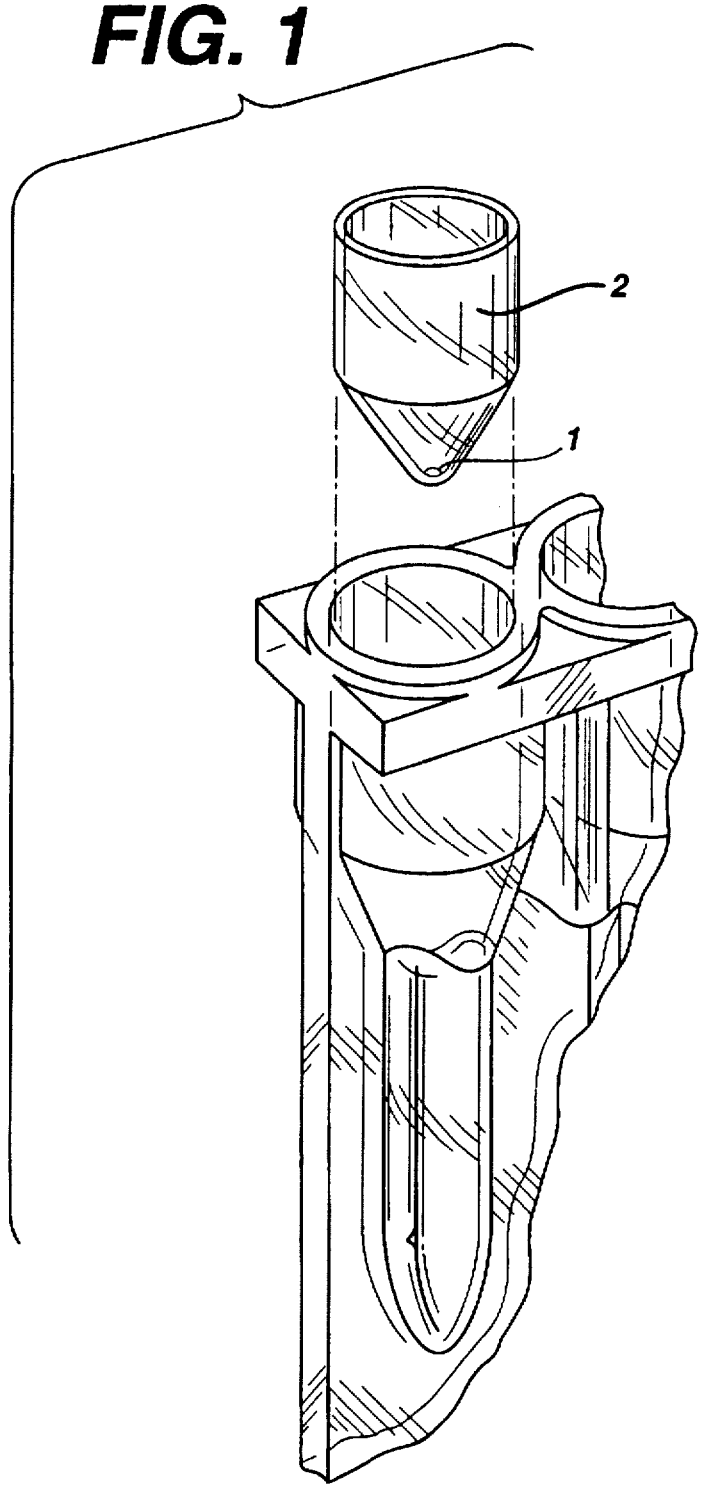
FIG. 1 shows a reaction and separation vessel with an insert having a narrow aperture placed in the upper reaction chamber.
Figure 2:
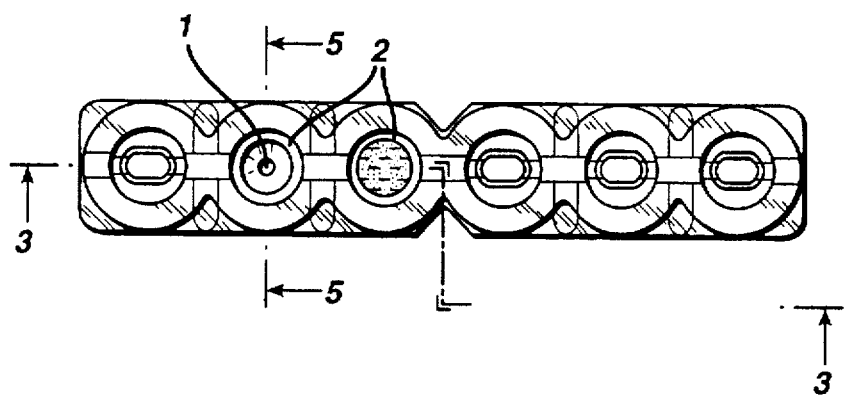
FIG. 2 is a top view of a cassette of six reaction vessels showing four vessels with no insert and one vessel (second from left) containing an insert as shown in FIG. 1, and one vessel (third from left) showing a vessel containing reactants.
Figure 3:
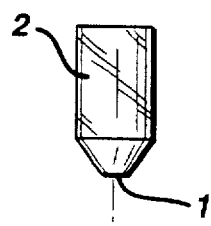
FIG. 3 is a cross-sectional view of a cassette of reaction vessels along the line 3—3 of FIG. 2.
Figure 3:
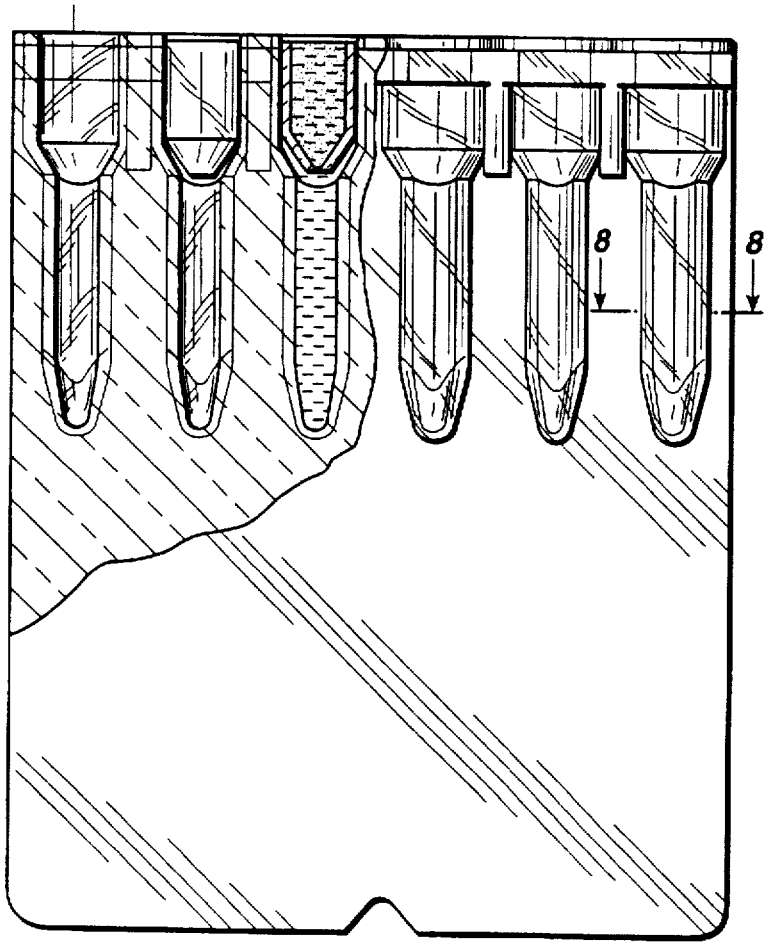
Figure 4:
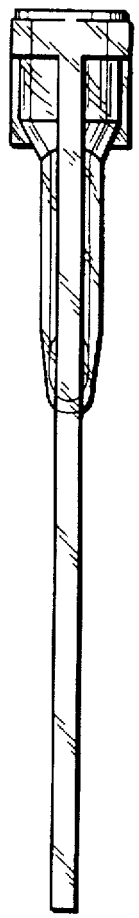
FIG. 4 is a side view of a cassette of reaction vessels.
Figure 5:
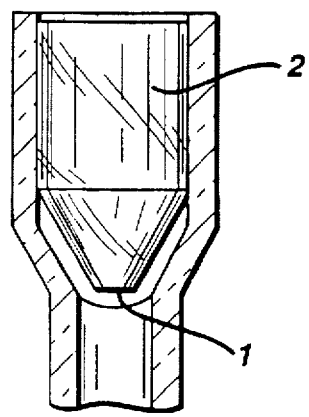
FIG. 5 is a cross-sectional view along the line 5—5 of FIG. 2, showing an insert with a narrow aperture inside the upper chamber of a reaction vessel.
Figure 6:
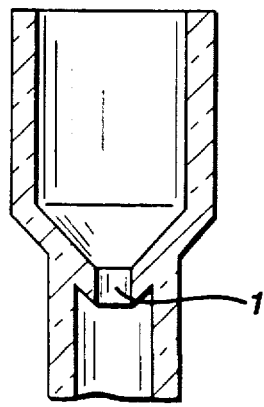
FIG. 6 shows the upper chamber of a reaction vessel constructed with a narrow aperture.
Figure 7:
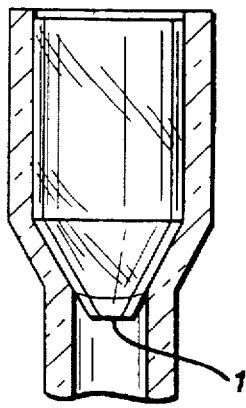
FIG. 7 shows an insert having an extended portion with an aperture disposed in the lower chamber.
Figure 8:
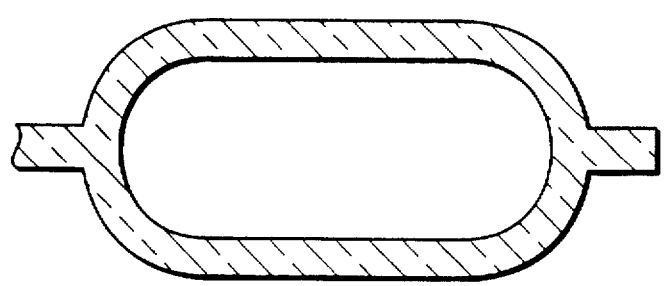
FIG. 8 is cross-sectional view along line 8—8 of FIG. 3.

The upper chamber of the vessel may be any shape and dimension useful for holding the reagents and sample while incubation is carried out. Typically, the upper chamber is cylindrical in the upper most portion. The barrier between the upper and lower chambers usually defines the lower boundary of the upper chamber and the upper boundary of the lower chamber. In a preferred embodiment, the barrier which forms the lower portion of the upper chamber is conical, with the apex extending toward or into the lower chamber, as shown in any of FIGS. 1, 5, 6, 7. A portion of the barrier is constructed to retain the reagents and sample of the upper chamber during incubation under normal gravity and atmospheric pressure conditions, while permitting fluid to flow from the first chamber to the second chamber when a force such as increased pressure or centrifugal force is applied. This may be accomplished by various means such as a small aperture, membrane, a plug, a constriction, an insert having any of several geometries, or screen, and any combination thereof. In a preferred embodiment, the barrier comprises an aperture having a diameter small enough to prevent passage of fluid from the first chamber to the second chamber under normal gravity or atmospheric pressure, while permitting fluid to flow under increased pressure. The aperture 1 is located at the apex of the conical portion of the upper chamber, either in an insert 2, as shown in FIGS. 1, 5, or 7, or integrally formed in the upper chamber as shown in FIG. 6.

The aperture may be of any diameter which is small enough such that surface tension of the fluid in the upper chamber will prevent flow from the upper chamber to the lower chamber under normal gravity or atmospheric pressure, while permitting surface tension to be overcome and, thus, facilitating passage of contents from the upper chamber to the lower chamber under increased pressure or gravity forces. The aperture diameter may be altered according the magnitude of the force used, i.e. smaller diameter when greater force is applied and larger diameter when a lesser force is applied. The diameter may also be altered to accommodate different sized particles in the reagents. In a preferred embodiment, the diameter of the aperture is in the range of about 0.010 to 0.050 inch. In a particularly preferred embodiment, the diameter of the aperture is 0.020 inch.

Figure 11:
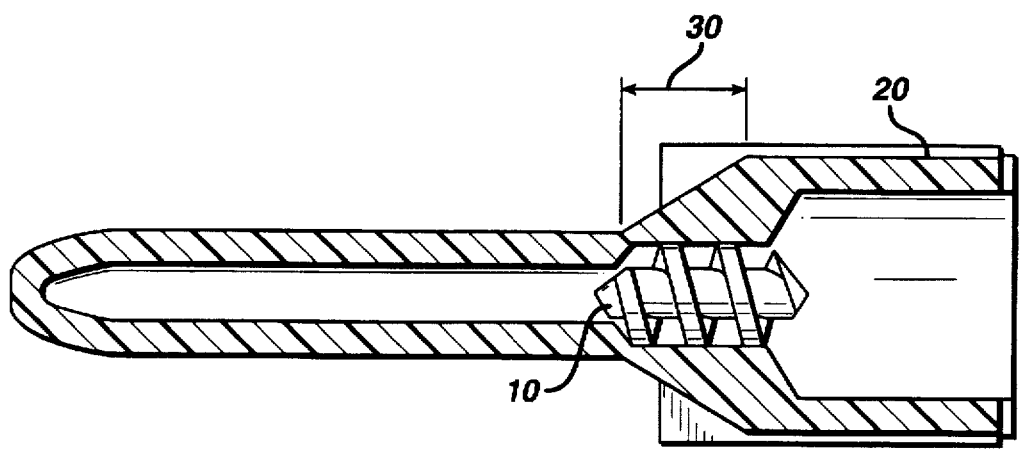
FIG. 11 shows a side view of a reaction and separation vessel with a spiral insert 1 placed in the upper chamber 2, the lower portion 3 of the upper chamber having been modified to accommodate said insert.

In another embodiment, the barrier means separating the upper and lower chambers comprises a spiral insert; such spiral may be in the configuration of a screw. The spiral is preferably round or cylindrical in diameter, although an oval configuration is also contemplated. Like the aperture described above, the passageway described by the shaft, the threads of the spiral, and the walls of the chamber has a diameter small enough to prevent passage of fluid from the upper chamber to the lower chamber under normal gravity or atmospheric pressure, while permitting fluid flow under increased force or pressure. A further function of the insert is to reduce the possibility of splashing of diluent or solution from the lower chamber into the upper chamber thereby contaminating the upper chamber. Such splashing may occur during shipping and handling, for instance. The spiral is located in the upper chamber at the base of upper chamber 3 as shown in FIG. 11, or may be integrally molded in such position with the reaction vessel.

In the case where the spiral insert is separately inserted into the upper chamber, the insert may be molded from any suitable material that will not interfere with the agglutination reaction or separation, or with any visualization of results, such as for example, glass or plastic. The material is preferably a plastic such as for example polypropylene, polyamides such as nylon, acetal resins such as Delrin™ or Delrin P™, crosslinked polystyrene/divinylbenzene such as Rexolite™, polycarbonates or polyethylenes. In a preferred embodiment, the material is polypropylene.

The spiral may be of any geometry such that surface tension of the fluid in the upper chamber will prevent flow from the upper chamber to the lower chamber under normal gravity or atmospheric pressure, while permitting surface tension to be overcome and, thus, facilitating passage of contents from the upper chamber to the lower chamber under increased pressure or gravity forces. For example, the pitch of the spiral threads may be at any angle that will permit passage of fluid (e.g., containing blood cells) under increased pressure from the upper to the lower chamber, while preventing contamination of upper chamber with fluid or matrix from the lower chamber. The pitch may be altered according the magnitude of the force used, i.e. smaller area described by spiral shaft and threads and chamber wall when greater force is applied and larger area when a lesser force is applied. The spiral geometry may also be altered to accommodate different sized particles in the reagents. Further, the insert enhances the prevention of splashing of column contents (diluent or solution containing separation matrix) into the upper chamber.

In the spiral insert embodiment of the invention, the number of threads per inch and thread depth will be limited only by the effectiveness of such resulting spiral in preventing contamination of the upper chamber with fluid from the lower chamber (at the lower end of the range), and by the ability of specimen, for example, red cells, to make passage down the spiral under increased pressure (at the higher end of the range). For the forgoing reason, and for ease of passage of red cells and other agglutinates which will passage through the barrier means, it is preferable for the threads, center shaft, and column walls describing the passageway to be relatively smooth in texture and finish. The walls of the thread portion of the spiral insert which appose the column wall may be either sharp or flat.

In a preferred embodiment, and for use in the current configuration of the BIOVUE™ cassette which comprises six reaction vessels, the spiral will have about 6 to about 30 threads per inch, more preferably about 12 to about 20 threads per inch, and a pitch measured in inches from top of one thread to top of next lower thread in the range of about 0.033 to about 0.166, more preferably about 0.050 to about 0.083.

The total diameter of the spiral insert is in the range of about 0.110 to about 0.140 inch, more preferably about 0.120 to about 0.130 inch.

Figure 12A:
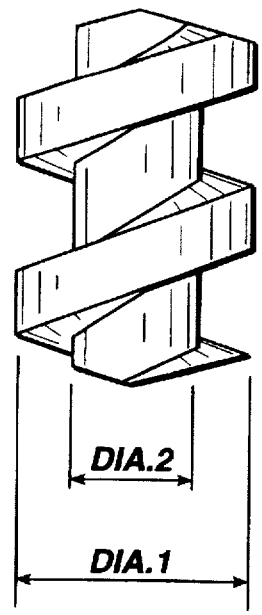
FIGS. 12A and 12B shows side views of spiral insert configurations; (A) shows an insert having a total diameter 1 of 0.120 inch and the inner shaft having a diameter 2 of 0.060 inch; (B) shows an insert having a total diameter 1 of 0.120 inch and the inner shaft having a diameter 2 of 0.080 inch.
Figure 12B:
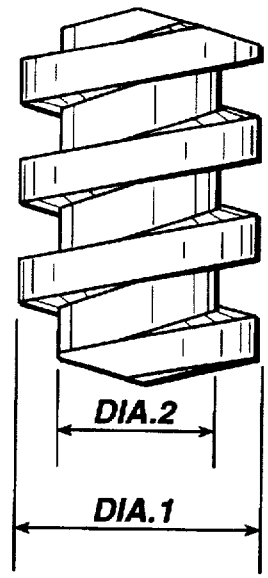
Figure 13:
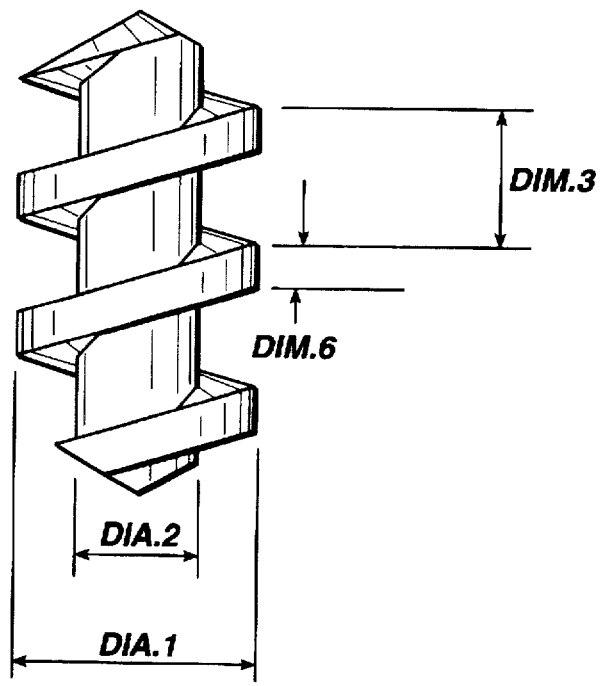
FIG. 13 shows a side view of spiral insert having a total diameter 1 of 0.120 inch and the inner shaft 2 having a diameter of 0.060 inch.

The shaft of the spiral insert is in the range of about 0.030 to about 0.090 inch, more preferably about 0.060 to about 0.080 inch. Reference is drawn to FIGS. 11, 12 and 13 describing examples of relative geometries of the insert components. With reference to FIG. 13, the approximate geometries (in inches) may be as follows:

| Threads/Inch | DIM 3 | DIM 6 |
| --- | --- | --- |
| 12 | .083 | .020 |
| 14 | .070 | .020 |
| 16 | .060 | .015 |

As an alternative to the round diameter spiral insert placed into the modified lower portion of the upper chamber as shown in FIG. 11, it is also herein provided an oval shaped spiral which may have similar geometry of pitch. As previously described for a round diameter spiral insert, the oval barrier means may take either the form of an insert or a spiral constriction molded in one unit with the chambers.

As a further alternative, a constricted passageway between the upper and lower chambers may be provided by sonic welding of the column after it has been loaded with reagents. Alternatively, the barrier may comprise a disk or plug of porous material located in the top of the lower chamber or column. The plug is in the form of a cylinder sized to fit between the upper and lower chambers, adapted to retard splash of the lower chamber contents (e.g., reagent and separation matrix) into the upper chamber. The porous plug is further adapted to prevent sample from passing through prematurely (e.g., prior to centrifugation), but through which the sample will pass under greater than atmospheric pressure (e.g., under centrifugation). The porous plug is constructed of any material that will not interfere with the agglutination reaction or separation, or with any visualization of results, or non-specifically bind to any of the components thereof, for example, glass, and more specifically, scintered glass, or plastic, for example, polypropylene.

Other suitable barriers may take the form of flanges fixed in a spiral, stepwise cascade around the inner wall of the chamber, or other similar tortuous path designs which will function as above-described in preventing contamination of upper chamber contents. The barrier may also take the form of a circular valve or diaphragm placed into the column. Such a diaphragm may, for example, have a center hole or perforation and be scored radially, from column wall to center perforation. Upon application of force, the diaphragm will open permitting sample contents to pass from the upper chamber to the lower chamber. The diaphragm will be constructed of any suitable material that will not interfere with the agglutination reaction or separation, or with any visualization of results. The diaphragm will be constructed of any suitable flexible, pliable material, such as for example silicone rubber.

When a vessel of the present invention is used to accomplish an agglutination reaction and separation, reagents and sample are added to the upper chamber for incubation. The barrier retains the sample and reagents in the upper chamber while the incubation occurs. In a preferred embodiment, where the barrier has an aperture, or wherein it is in the form of a spiral insert, the diameter of the aperture or the geometry of the spiral, respectively, is small enough that surface tension of the liquid and sample across the aperture or spiral will retain the contents in the upper chamber under normal gravity and atmospheric pressure. After sufficient incubation time, a force is applied by any of various means, such as by centrifugation, pressure, or suction, against the barrier in a direction substantially along the axis from the upper chamber to the lower chamber. The force must be sufficient to overcome the barrier and allow passage of the contents of the upper chamber into the lower chamber. In a preferred embodiment, where the barrier comprises an aperture, or wherein the barrier means comprises a spiral insert, surface tension is overcome by the force, and the contents flow from the upper chamber into the lower chamber to the separation matrix.

The barrier is also important in providing a means to reduce contamination of the upper chamber with diluent or solution in the lower chamber, such as may otherwise occur by splashing or other disturbance during shipping and handling.

Figure 14:
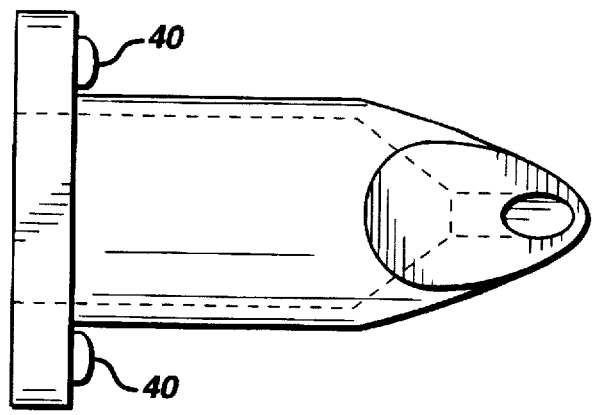
FIG. 14 shows one cell of a liner designed to fit into the upper chamber of a reaction vessel column. Each conical member or cell has o-ring 1 located around the cell below the liner body.
Figure 15:
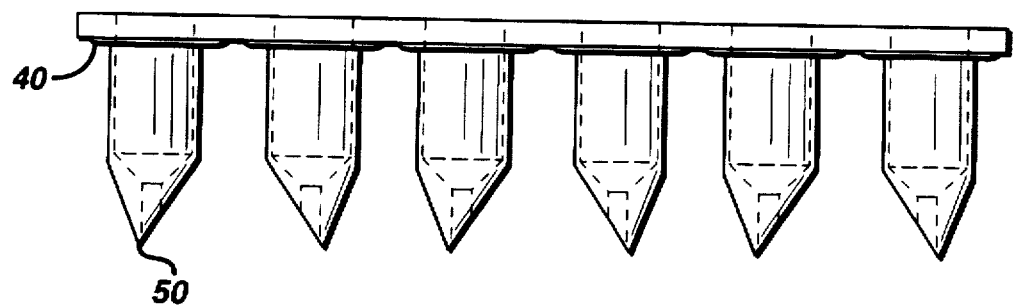
FIG. 15 shows a liner comprising six conical members or cells having pointed apexes designed to fit into the upper chambers of a cassette having six reaction vessel columns. Each member has o-ring 1 surrounding the member below the liner body. Each member further has apex 2 adapted for piercing a foil seal covering the reaction vessel columns of the cassette.

A further embodiment of the invention is a liner which may be inserted into the top of the reaction vessel just prior to sample addition. Such liner comprises a body and one or preferably a plurality of members or cells depending from the body, such cells having a conical or funnel shape. The narrowed apex of the cell, containing an aperture, when inserted into the cassette, is oriented toward the inside of the vessel, as shown in FIGS. 14 and 15. The liner can be used in vessels with or without barrier means such as crimps or inserts. In a preferred embodiment, the liner comprises a cell having an aperture with a diameter (1) small enough to contain the specimen being delivered to the vessel until the vessel is subjected to force (e.g., by centrifugation), provided the incubation time is not extended by any insulating effect of the air gap between the apex and the separation matrix in the column; or (2) large enough to allow the specimen being delivered to readily pass into the reaction vessel chamber, provided the test system can tolerate early contact with reagent splash. The cells of the liner preferably have a sealing means located at a position spaced from the narrowed apex, e.g., at the outside tops thereof, just below the liner body. Reference is made to FIGS. 14 and 15 in this regard. The sealing means is a raised ring preferably integral with the liner. The liner cell fits into the reaction vessel upper chamber such that it will not become easily dislodged during normal handling. The raised ring or o-ring will come to rest against a margin around the vessel on the upper surface of the cassette, thus sealing a junction between the liner and cassette. The raised ring or o-ring prevents capillary action of any splashed column contents from one column to another.

As discussed hereinabove, in the absence of an insert provided in the vessels, diluent or solution containing separation matrix may enter the upper chamber during shipping and handling. In such instance, and wherein the separation matrix may also contain antibodies or other reagents that will directly affect the result of a test, such splashing can result in cross-contamination of a column with reagent from other columns. This may occur when the user inserts a pipette tip into the reaction vessel upper chamber, contaminating the tip with splashed reagent, which may then be transferred to another vessel on the pipette. The latter may lead to false results in the agglutination assay.

The purpose of the liner is to prevent cross-contamination of reagent from one vessel to the next during pipetting; which reagent may have splashed up into the upper chamber during shipping and handling.

The liner may take the form of a single conical member or cell, to be individually placed atop each reaction vessel. In a preferred embodiment, however, and with reference to FIG. 15, the liner takes the form of a single unit having six such conical cells arranged side-by-side, integral with the body of the liner. Such a configuration permits a single liner unit containing six individual cells to be placed atop a six reaction vessel BIOVUE™ cassette.

With reference to FIGS. 14 and 15, each conical cell of the liner has a narrowed, pointed apex with an aperture therethrough. As the BIOVUE™ vessels are provided as a cassette comprising six columns, sealed across the tops thereof by a foil strip, under manual pressure the pointed apexes of the liner will puncture the foil seal over all six columns. The specimen sample(s) may then be delivered via pipette directly into the cells. The clean liner cells are thus free of any contaminating reagent or separation matrix which may otherwise contact the specimen and be carried over to another column.

The liner is conveniently inserted into the columns by the end-user manually or by use of a pronged tool. For insertion of a six-cell liner into a BIOVUE™ cassette, the cassette foil is punctured with the liner tips and completely inserted by a rocking motion of the liner. Use of a pronged tool assists alignment of liner and cassette during insertion. As the liner body is conveniently the same area and shape as the top surface of the cassette, the liner may conveniently remain in place during processing of the cassette. Use of liners in this manner does not interfere with assay performance or results (e.g., centrifugation, free passage of non-agglutinated red cells through separation matrix, and entry of agglutinated red cells into the column). However, columns without o-rings did not prevent cross-column reagent contamination during use. See Examples 10 and 11 for comparative functional tests of liners with and without o-rings. The results therein demonstrate o-rings prevent cross-column reagent contamination which can be due to reagent "wicking" between cassette foil and liner with resulting flow of reagent across the cassette top.

The liner and cells thereof may be made of any suitable material that will not interfere with the agglutination reaction or separation, such as for example glass or plastic. The material must be suitable for puncturing the foil seal on the cassette. To allow for efficient delivery of sample to the upper chamber from the liner cell, it is preferable that the liner cell wall be relatively smooth in texture and finish. The material is preferably a plastic such as for example polyester, acetal, acrylic, acrylon nitrile butadiene styrene (ABS), nylon, polycarbonate, polyamide or polypropylene. In a preferred embodiment, the material is acrylic.

In the Biovue™ system, incubation of 10 µl reagent red cell in 40 µl patient's serum, together with 40 µl of low ionic strength solution occurs in the upper chamber for 10 minutes to allow presumptive patient's IgG antibody to bind to red cell surface antigen(s). These assay components are added separately and it is important that they remain in the upper chamber so that they can mix, providing a constant ratio of low ionic strength solution to red cells to serum from assay to assay. The barrier serves to facilitate this under normal gravitational force and pressure. It also serves to reduce the chance of any of the assay components being forced into the lower chamber during sample addition. The barrier also enables the assay components to remain in the upper chamber throughout the incubation period.

The barrier is also important to prevent premature binding of the anti-human IgG antibodies to the presumptive anti-red cell antibodies in the patient serum before they have bound to red cells, reducing the chance of agglutination ultimately taking place in the lower chamber. After incubation, centrifugal force is applied to move the contents of the upper chamber through the barrier into the lower chamber which contains anti-human IgG which binds to the patient's IgG on the surface of the reagent red cells causing agglutinates to form which do not pass through the matrix to the bottom of the lower chamber.

The following examples are provided for purposes of illustration only and not by way of limitation of the scope of the invention.

EXAMPLE 1

BIOVUE™ columns with inserts were compared to columns without inserts to determine the efficacy of each configuration for maintaining the air space that separates the reactants from the separation matrix during the incubation period. Inserts having an aperture of 0.040 inch were used. 40 microliters of buffer solution were added to each of the 840 columns tested. A manual pipette held at approximately a 45 degree angle from the vertical axis of the column was used to deliver the 40 microliters. The columns were then observed to determine whether the air space beneath the reaction chamber was maintained. The number of "breakthroughs" is given in Table 1.

TABLE 1

|  | Number of Tests | Number of Breakthroughs | Percentage of Breakthroughs |
| --- | --- | --- | --- |
| Columns with Inserts | 840 | 0 | 0% |
| Columns Without Inserts | 840 | 231 | 27.5% |

EXAMPLE 2

Reagents were also added to columns (with and without inserts) and incubated for 10 minutes at 37° C. 40 microliters of buffer, 40 microliters of serum, and 10 microliters of red cell suspensions were added to each of the 480 columns tested. A pipette held at approximately a 45 degree angle was used to deliver the reactants. After the incubation period, the columns were inspected to determine whether the air space beneath the reaction chamber was maintained. The frequency of "break throughs" is given in Table 2.

TABLE 2

|  | Number of Tests | Number of Breakthroughs | Percentage of Breakthroughs |
| --- | --- | --- | --- |
| Columns with Inserts | 480 | 0 | 0% |
| Columns Without Inserts | 480 | 16 | 3.3% |

EXAMPLE 3

Columns were filled with 40 microliters of buffer using an automatic pipette held at about a 45 degree angle. Automatic pipettes typically deliver with more force than do manually operated models. Observations were made after filling, to determine if the air space beneath the reaction chamber was maintained. Results in columns with and without inserts are given in Table 3.

TABLE 3

|  | Number of Tests | Number of Breakthroughs | Percentage of Breakthroughs |
| --- | --- | --- | --- |
| Columns with Inserts | 240 | 0 | 0% |
| Columns Without Inserts | 240 | 103 | 43% |

EXAMPLE 4

240 columns were filled with 40 microliters of buffer using a single pipette held vertically. By holding the pipette vertically, the fluid is forced against the aperture with greater pressure and thus is more likely to break the air space separating the reaction chamber from the separation chamber. The results of this experiment are given in Table 4.

TABLE 4

|  | Number of Tests | Number of Breakthroughs | Percentage of Breakthroughs |
| --- | --- | --- | --- |
| Columns with Inserts | 240 | 0 | 0% |
| Columns Without Inserts | 240 | 144 | 60% |

EXAMPLE 5

The reaction chambers of 240 columns were also filled with 40 microliters of buffer using an automatic pipette held vertically, which is more likely to cause breaching of the air space beneath than when the automatic pipette is held at an angle. The results of these tests using columns with inserts and columns without inserts are given in Table 5.

TABLE 5

|  | Number of Tests | Number of Breakthroughs | Percentage of Breakthroughs |
| --- | --- | --- | --- |
| Columns with Inserts | 240 | 0 | 0% |
| Columns Without Inserts | 240 | 204 | 85% |

In addition to maintaining the air space between the reaction chamber and the separation matrix during the incubation phase of the test, the invention functions also as a means to prevent splashing that may occur during shipping and handling in which part of the contents of the lower separation chamber may splash up into the upper reaction chamber. To test the efficacy of splash prevention, cassettes with and without inserts were shipped from New Jersey to California and back. Shipping was by way of air and land included loading, unloading, and delivery to the laboratory. The method used was common for this product line. After the return shipment, the cassettes were examined for the presence of splashed liquid in the reaction chambers. Results are given in Table 6.

TABLE 6

|  | Number of Tests | Number of Columns with Splashes | Percentage of Columns with Splashes |
| --- | --- | --- | --- |
| Columns with Inserts | 816 | 30 | 3.7% |
| Columns Without Inserts | 768 | 571 | 74.3% |

EXAMPLE 7

An additional shipping study was conducted to test for splash reduction with inserts having apertures of diminishing size. The openings between the reaction chamber and the separation matrix were 0.025, 0.020, and 0.015 inches in diameter. 600 columns were fitted with each of these inserts. The control had no inserts. The cassettes were packaged and subjected to an in-house surrogate shipping study in which the box was dropped 10 times from a height of 3 feet. The angle of the box was controlled so that the container dropped on all 6 of its flat surfaces as well as on 1 corner and on 3 edges. This standardized test represents the worst case for shipping and handling. The results given in Table 7 show the inverse relationship between aperture size and splash reduction.

TABLE 7

|  | Number of Tests | Number of Columns with Splashes | Percentage of Columns with Splashes |
| --- | --- | --- | --- |
| Columns with .015 Inserts | 600 | 75 | 13% |
| Columns with .020 Inserts | 600 | 120 | 20% |
| Columns with .025 Inserts | 600 | 132 | 22% |
| Columns without Inserts | 600 | 600 | 100% |

EXAMPLE 8

Another means by which the orifice between the reaction chamber and the separation chamber below can be diminished is by "crimping" the cassette. This can be achieved by impact extrusion in which the neck of the cassette just beneath the reaction chamber is impacted. The force and duration of the impact determines the degree to which the opening is diminished. The shape of the impacting tool determines the form of the opening. Several configurations are possible. The crimping process can be accomplished in the production line after the columns have been loaded with reagents and glass beads.

Figure 9:
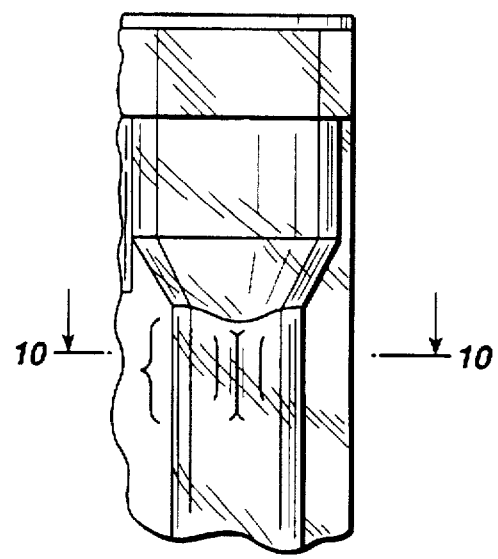
FIG. 9 shows a reaction and separation vessel which has been crimped just below the upper chamber.
Figure 10:
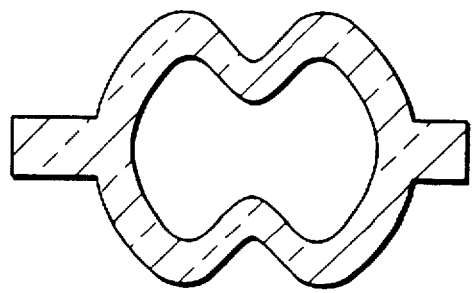
FIG. 10 is a cross-sectional view along line 10—10 of FIG. 9.

816 columns from the manufacturing line were crimped, as described above in order in constrict the opening between the reaction chamber and the separation matrix. The crimp resulted in the cross-sectional shape shown in FIG. 10, through the region indicated by a bracket in FIG. 9. These, along with 768 uncrimped controls were packaged and shipped to and from California as previously described. The reduction of splashes into the reaction chambers caused by the shipping conditions is given in Table 8.

TABLE 8

|  | Number of Tests | Number of Chambers with Splashes | Percent of Chambers with Splashes |
| --- | --- | --- | --- |
| Columns with Crimps | 816 | 548 | 67% |
| Columns with No Crimps | 768 | 571 | 74% |

EXAMPLE 9

Spiral insert barrier means can be used to restrict the size of the orifice between the reaction (upper) chamber and the separation (lower) chamber. A spiral insert is molded from polypropylene and inserted into the neck of the cassette just beneath the modified upper chamber. The spiral insert is placed into the neck of the cassette during the production process after the columns have been loaded with reagents and separation matrix (e.g., glass beads).

EXAMPLE 10

BIOVUE™ columns with liners having o-rings were compared to columns with liners without o-rings, to determine whether o-rings prevented cross-column reagent contamination.

Cassettes were mock shipped to create splash in the upper chamber and on the foil by tapping or striking the cassette against a solid work surface.

One hundred ninety two (192) cassettes with liners having no o-rings were observed for column reagent wicking after insertion into cassette columns. Half the liners (96) were inserted into cassettes manually and the other half by use of a two-pronged tool discussed above.

Three hundred thirty six (336) cassettes with liners having o-rings were observed for column reagent wicking as above. One-half (168) cassettes were inserted with liners manually, and 168 were inserted using a two-pronged tool.

Column wicking was assessed visually by examining the top side of the cassette. Wicking was determined by observation of reagent fluid between the cassette foil top and the underside of the liner body.

Table 9 shows the number and percentage of cassettes with wicking per total number of cassettes tested. The method of liner insertion did not affect the results using the liner having the o-ring, but did affect the results using the liner without o-ring. As shown, when the liners were inserted manually (cassettes in inverted position), the number of cassettes with wicked reagent was about double the number as when the liners were inserted with the tool (cassettes in upright position).

TABLE 9

| Liner Insertion Method | Liner Without O-Rings | Liner With O-Rings |
| --- | --- | --- |
| Tool | 39/96 (40.6%) | 0/168 |
| Manual | 74/96 (77.1%) | 0/168 |

EXAMPLE 11

Cassettes with liners having no o-rings were compared in a functional test to cassettes with liners having o-rings.

Cassettes were mock shipped to create reagent splash in the upper chamber and on the foil as described in Example 10.

Liners were inserted into cassette columns both manually and using the two-pronged tool as described hereinabove. In half the cassettes, ten (10) uL of 4% RBC (in normal saline) was pipetted into each column using the BIOVUE™ BioHit (Ortho Diagnostic Systems Inc., Raritan N.J.) pipette. In the other half of cassettes, 50 µL of 0.8% RBC (in normal saline) having surface antigen as specified in Table 10 below, was pipetted into the cassette columns. In half the cassettes tested, the Ortho BIOVUE™ ABE International cassette (Ortho Diagnostic Systems Inc., Raritan, N.J.) was used; in the other half of cassettes tested, the Ortho BIOVUE™ RHK cassette (Ortho Diagnostic Systems Inc., Raritan, N.J.) was used. The ABE and RHK cassettes are prepared with antibodies in respective columns as shown in Table 10 below.

TABLE 10

| ABE CASSETTE | | |
| --- | --- | --- |
| column | antibody | Expected Result With $A_1\pi$ Cells |
| 1 | anti-A | + |
| 2 | anti-B | − |
| 3 | anti-AB | + |
| 4 | anti-D | − |
| 5 | anti-CDE | − |
| 6 | control (diluent) | − |

| RHK CASSETTE | | |
| --- | --- | --- |
| column | antibody | Expected Result With $R_1R_1K(-)$ Cells |
| 1 | anti-C | + |
| 2 | anti-E | − |
| 3 | anti-c | − |
| 4 | anti-e | + |
| 5 | anti-K | − |
| 6 | control (diluent) | − |

When ABE cassettes were used, $A_1\pi$ cells were used as sample. When RHK cassettes were used, $R_1R_1K(-)$ cells were used as sample. Pipetting was done from the leftmost cassette column to the right. Cassettes were centrifuged in the Ortho BIOVUE™ Centrifuge (Ortho Diagnostic Systems Inc., Raritan N.J.) for 2 minutes at 794+/−16 xg, then for 3 minutes at 1510+/−30 xg. Each column with a negative reaction (non-agglutination of RBCS) was evaluated for complete free passage of red cells through the entire column.

A false positive reaction will occur if, for example, anti-A antibody from column 1 of the ABE cassette is transferred to column 2, and the cells now react in column 2.

Results are shown in Table 11. In columns with the o-ring, all expected positive reactions were positive. However, all expected negative reactions were not negative. There was one false positive result. The cause, while not identified, was not reagent wicking. Table 11 shows the number and percentage of cassettes and columns with false positive reaction per total number of cassettes tested. The method of liner insertion did not affect the results using the liner with o-rings, but did indirectly affect the results using the liner without o-rings, because all false positive results were in cassettes with visible wicked reagent.

TABLE 11

| Liner Insertion Method | | Liner Without O-Rings | Liner With O-Rings |
| --- | --- | --- | --- |
| Tool | Cassettes | 1/96 (1%) | 1/96 (1%) |
| (Upright) | Columns | 1/384 (0.3%) | 1/384 (0.3%) |
| Manual | Cassettes | 9/96 (10%) | 0/96 |
| (Inverted) | Columns | 10/384 (2.6%) | 0/384 |
| Total | Cassettes | 10/192 (5.2%) | 1/192 (0.5%) |
|  | Columns | 11/768 (1.4%) | 1/768 (0.1%) |

What is claimed is:

1. A liner for preventing cross-contamination of reagent or solution from one column of an agglutination assay cassette to another column of said cassette, wherein said liner comprises a body and at least one conical member depending therefrom, wherein said conical member has an aperture at a narrowed apex thereof, and wherein said conical member has sealing means located at a position spaced from said narrowed apex.

2. The liner of claim 1 wherein the conical member comprises a first end comprising said narrowed apex and a second end spaced therefrom adjacent to said body, wherein said sealing means is located at or adjacent to said second end.

3. The liner of claim 2 wherein the sealing means comprises an o-ring surrounding said conical member.

4. The liner of claim 3 wherein the sealing means comprises an o-ring integral with said conical member.

5. The liner of claim 4 comprising six conical members linearly depending from said body.

6. The liner of claim 5 sized to fit in the columns of the agglutination assay cassette.

7. The liner of claim 6 wherein the liner is acrylic.

8. A liner comprising a body and six conical members depending therefrom, wherein each conical member comprises a first end spaced from said body and having an aperture at a narrowed apex thereof and a second end spaced from said first end having an o-ring surrounding and integral with said conical member.

9. A foil sealed cassette comprising six reaction vessels linearly arranged therein, and a liner comprising a body and six conical members linearly depending therefrom, wherein the conical members comprise a narrowed apex capable of puncturing said foil seal, and when inserted such liner is frictionally engaged in said cassette so as to seal a junction between the cassette and the liner.

10. The foil sealed cassette and liner of claim 9 wherein the means for sealing said junction is o-rings surrounding each of said conical members and integral with each of said conical members.

* * * * *